(12) United States Patent
Wang et al.

(10) Patent No.: US 8,128,621 B2
(45) Date of Patent: Mar. 6, 2012

(54) IRRIGATED ABLATION ELECTRODE ASSEMBLY AND METHOD FOR CONTROL OF TEMPERATURE

(75) Inventors: Huisun Wang, Maple Grove, MN (US);
Jeremy D. Dando, Plymouth, MN (US);
Harry Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1131 days.

(21) Appl. No.: 11/948,362

(22) Filed: Nov. 30, 2007

(65) Prior Publication Data
US 2008/0071267 A1     Mar. 20, 2008

Related U.S. Application Data

(63) Continuation-in-part of application No. 11/434,220, filed on May 16, 2006, now Pat. No. 7,857,810.

(51) Int. Cl.
*A61B 18/14*     (2006.01)
(52) U.S. Cl. .......................................................... 606/41
(58) Field of Classification Search ...................... 606/41
See application file for complete search history.

(56) References Cited

U.S. PATENT DOCUMENTS
5,061,823 A     10/1991     Carroll
(Continued)

FOREIGN PATENT DOCUMENTS
WO     WO-0103589     1/2001
(Continued)

OTHER PUBLICATIONS

"Saline-Irrigated Radiofrequency ablation eoectrode with external cooling", Wittkampf, et al., Journal of Cardiovascular Electrophysiology, vol. 16, Mar. 3, 2005.

*Primary Examiner* — Lee Cohen
(74) *Attorney, Agent, or Firm* — Dykema Gossett PLLC

(57) ABSTRACT

Embodiments of the present invention provide an irrigated catheter having irrigation fluid directed at target areas where coagulation is more likely to occur so as to minimize blood coagulation and the associated problems. In one embodiment, an irrigated ablation electrode assembly for use with an irrigated catheter device comprises a proximal member having at least one passageway for a fluid with an outlet disposed at an external surface of the proximal member; and a distal member connected with the proximal member and having an external surface. The distal member includes an electrode. The external surface of the proximal member and the external surface of the distal member meet at an intersection. The at least one passageway of the proximal member is configured to direct a fluid flow through the outlet toward a region adjacent the intersection.

24 Claims, 6 Drawing Sheets

U.S. PATENT DOCUMENTS

| | | |
|---|---|---|
| 5,456,682 A | 10/1995 | Edwards et al. |
| 5,545,161 A | 8/1996 | Imran |
| 5,688,267 A | 11/1997 | Panescu et al. |
| 5,989,249 A | 11/1999 | Kirwan, Jr. |
| 6,017,338 A * | 1/2000 | Brucker et al. ............. 606/41 |
| 6,662,034 B2 | 12/2003 | Segner et al. |
| 6,757,565 B2 | 6/2004 | Sharkey et al. |
| 6,977,469 B2 | 12/2005 | Seinen et al. |
| 7,591,816 B2 * | 9/2009 | Wang et al. ................. 606/41 |
| 2004/0054272 A1 | 3/2004 | Messing |
| 2004/0267106 A1 | 12/2004 | Segner et al. |
| 2005/0177151 A1 * | 8/2005 | Coen et al. .................. 606/41 |
| 2005/0267467 A1 | 12/2005 | Paul et al. |
| 2006/0287650 A1 | 12/2006 | Cao et al. |
| 2007/0270791 A1 | 11/2007 | Wang et al. |
| 2008/0045943 A1 * | 2/2008 | Wittkampf et al. ............ 606/41 |
| 2008/0161794 A1 | 7/2008 | Wang |

FOREIGN PATENT DOCUMENTS

| | | |
|---|---|---|
| WO | 2005048858 | 6/2005 |
| WO | 2005112814 A2 | 12/2005 |
| WO | WO-2009023385 | 2/2009 |
| WO | WO-2009152151 | 12/2009 |

* cited by examiner

IRRIGATED ABLATION ELECTRODE ASSEMBLY AND METHOD FOR CONTROL OF TEMPERATURE

CROSS-REFERENCE TO RELATED APPLICATIONS

The present application is a continuation-in-part of U.S. patent application Ser. No. 11/434,220, filed May 16, 2006, now U.S. Pat. No. 7,857,810. This application is related to U.S. patent application Ser. Nos. 11/646,237, now U.S. Pat. No. 7,824,406; Ser. No. 11/646,255, now U.S. Pat. No. 7,951,143; Ser. No. 11/646,275, now pending; and Ser. No. 11/646,270, now U.S. Pat. No. 7,591,816, all filed on Dec. 28, 2006. The entire disclosures of the above applications are incorporated herein by reference.

BACKGROUND OF THE INVENTION

1. Field of the Invention

The present invention pertains generally to ablation electrode assemblies. More particularly, the present invention is directed toward ablation electrode assemblies for use in the human body having a mechanism for irrigating targeted areas. The present invention also relates to methods for improved assembly and accurate measurement and control of the electrode temperatures while effectively irrigating the targeted areas.

2. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

Because RF ablation may generate significant heat, which if not carefully monitored and/or controlled can result in protein denaturation, blood coagulation, excess tissue damage, such as steam pop, tissue charring, and the like, it is desirable to monitor the temperature of the ablation assembly. It is further desirable to include a mechanism to irrigate certain target areas with biocompatible fluids, such as saline solution. This irrigation reduces or avoids excess, unwanted tissue damage, and blood coagulation and problems associated therewith. However, introduction of this irrigation solution may inhibit the ability to accurately monitor and/or control the temperature of the ablation assembly during use.

There are typically two classes of irrigated electrode catheters, open and closed irrigation catheters. Closed ablation catheters typically circulate a cooling fluid within the inner cavity of the electrode. Open ablation catheters, on the other hand, typically deliver the cooling fluid through open orifices on the electrode. Examples of these known catheters include the THERMOCOOL brand of catheters marketed and sold by Biosense-Webster. The current open irrigated ablation catheters use the inner cavity of the electrode, or distal member, as a manifold to distribute saline solution. The saline thus flows directly through the open orifices of the distal electrode member. This direct flow through the distal electrode tip lowers the temperature of the distal tip during operation, rendering accurate monitoring and control of the ablative process more difficult.

In these open electrode irrigated catheters, it has been determined that insulating the irrigation channels from the ablation electrode is beneficial. One such example was published on or around Mar. 2005 in an article entitled "Saline-Irrigated Radiofrequency Ablation Electrode with Electrode Cooling," by Drs. Wittkampf and Nakagawa et al., the content of which is hereby incorporated by reference in its entirety. Similarly, the content of PCT International Publication No. WO 05/048858, published on Jun. 2, 2005, is hereby incorporated by reference in its entirety.

BRIEF SUMMARY OF THE INVENTION

Embodiments of the present invention provide an irrigated catheter having irrigation fluid directed at target areas where coagulation is more likely to occur so as to minimize blood coagulation and the associated problems. The invention further provides for significant improvements over known irrigation catheters, including those disclosed by Drs. Wittkampf and Nakagawa et al., by providing a multiple piece irrigated ablation electrode assembly that has the advantages of irrigating the target area while simultaneously improving the operation, temperature response, temperature monitoring and/or control mechanisms of the ablation assembly, so as to prevent unwanted, unnecessary tissue damage and blood coagulation. The present invention also provides for ablation electrode assemblies that are easier to manufacture and assemble than known irrigated ablation electrode assemblies.

The present invention is directed to improved irrigated ablation electrode assemblies and methods useful in conjunction with irrigated catheter and pump assemblies and RF generator assemblies designed to monitor and control the ablation process while minimizing blood coagulation and unnecessary tissue damage.

In accordance with an aspect of the present invention, an irrigated ablation electrode assembly for use with an irrigated catheter device comprises a proximal member having at least one passageway for a fluid with an outlet disposed at an external surface of the proximal member; and a distal member connected with the proximal member and having an external surface, the distal member including an electrode. The external surface of the proximal member and the external surface of the distal member meet at an intersection. The at least one passageway of the proximal member is configured to direct a fluid flow through the outlet toward a region adjacent the intersection.

In some embodiments, the proximal member comprises a material having a thermal conductivity which is lower than a thermal conductivity of a material of the distal member. The distal member comprises an electrically conductive material. The proximal member comprises an electrically nonconductive material. The at least one passageway extends toward the distal member at an angle which is greater than 0 degree and less than 90 degrees, preferably between approximately 15 degrees and approximately 70 degrees, with respect to a longitudinal axis of the proximal member. The proximal member comprises a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof. The distal member comprises a material selected from the group consisting of platinum, gold, iridium, stainless steel, palladium and mixtures thereof.

In specific embodiments, the distal member includes a distal flow path extending along a longitudinal axis of the distal member. An insulative lining surrounds the distal flow path and separates the distal flow path from the distal member. The insulative lining comprises a material having a thermal conductivity which is lower than a thermal conductivity of a material of the distal member. The insulative lining comprises a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof. At least one temperature sensor disposed in the distal member. A pressure sensor is disposed inside the irrigation ablation electrode in a region in fluidic communication with the at least one passageway of the proximal member. The proximal member includes a plurality of passageways distributed generally uniformly in a circumferential direction of the proximal member. The at least one passageway of the proximal member does not come into contact with any interior portion of the distal member.

In some embodiments, the distal member has an external surface that includes a rounded distal portion that is non-spherical and a circular cylindrical proximal portion. Alternatively, the distal member has an external surface that includes a generally elliptical distal portion and a tapered proximal portion narrowing toward the proximal member. Alternatively, the distal member has an external surface that includes a generally spherical distal portion and a proximal neck portion that is circular cylindrical and narrower than the generally spherical distal portion. Alternatively, the distal member has an external surface that includes a generally flat tip surrounded by a rounded edge portion and a circular cylindrical proximal portion. Alternatively, the distal member has an external surface that includes a generally flat tip surrounded by a chamfered edge portion and a circular cylindrical proximal portion.

In accordance with another aspect of the invention, an irrigated ablation electrode assembly for use with an irrigated catheter device comprises a proximal member having an external surface; a distal member connected with the proximal member and having an external surface, the distal member including an electrode; and at least one passageway within the irrigated ablation electrode having an outlet for a fluid. The external surface of the proximal member and the external surface of the distal member meet at an intersection. The at least one passageway is configured to direct a fluid flow through the outlet toward a region adjacent the intersection.

In accordance with another aspect of the present invention, a method for irrigated ablation of tissue comprises flowing a fluid to an irrigated ablation electrode assembly which includes a proximal member having at least one passageway for the fluid with an outlet disposed at an external surface of the proximal member, and a distal member connected with the proximal member and having an external surface, the distal member including an electrode, wherein the external surface of the proximal member and the external surface of the distal member meet at an intersection; and directing the fluid flow through the at least one passageway of the proximal member through the outlet toward a region adjacent the intersection.

A technical advantage of the present invention is that the electrode assembly thermally separates the cooling irrigation fluid from the distal electrode, as well as from the temperature sensing mechanism(s) within the distal member, thereby allowing for improved temperature control and/or monitoring while simultaneously allowing for irrigation of the target areas to minimize coagulation and unwanted tissue damage. The separation of the cooling fluid from the temperature sensing mechanisms further allows for better monitoring of rising temperature of the electrode assembly during operation, as well as other tell-tale factors of over-ablation of targeted tissue areas.

The foregoing and other aspects, features, details, utilities, and advantages of the present invention will be apparent from reading the following description and claims, and from reviewing the accompanying drawings.

DETAILED DESCRIPTION OF EXEMPLARY EMBODIMENTS

In general, the instant invention relates to irrigated ablation electrode assemblies, and to methods of manufacturing and using such irrigated ablation electrode assemblies. For purposes of this description, similar aspects among the various embodiments described herein will be referred to by the same reference number. As will be appreciated, however, the structure of the various aspects may be different among the various embodiments.

Figure 1:
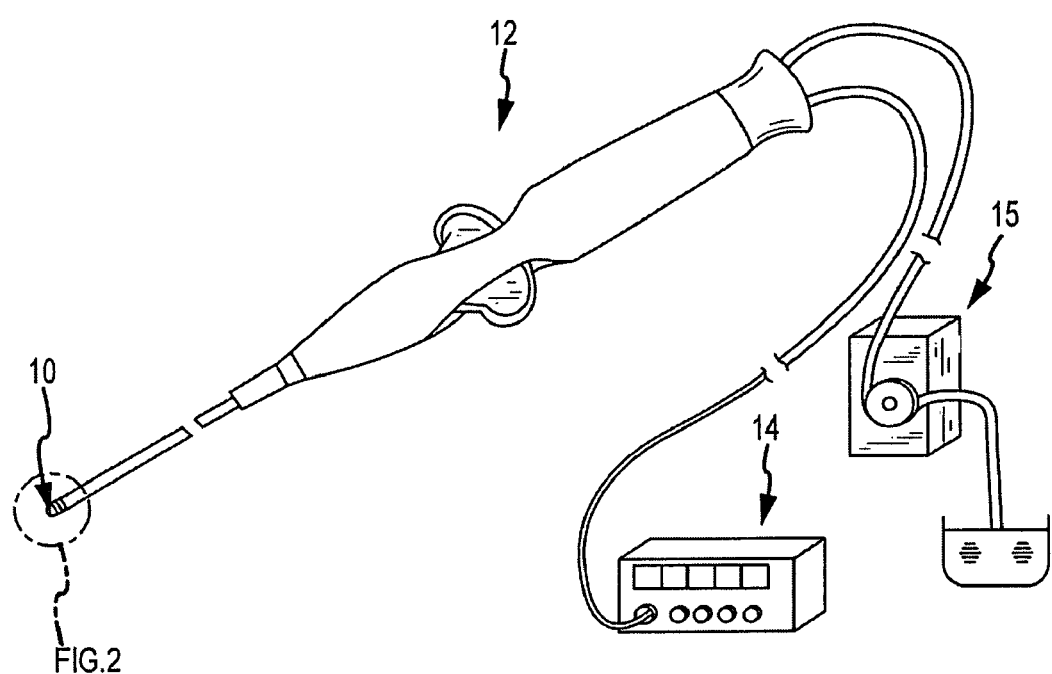
FIG. 1 is an isometric view of an ablation electrode assembly according to an embodiment of the present invention in conjunction with an irrigated catheter assembly operably connected to an RF generator assembly and a pump assembly.

As seen in FIG. 1, the ablation electrode assembly may comprise part of an irrigated ablation catheter 12 assembly, operably connected to a pump assembly 15 and an RF generator assembly 14 which serves to facilitate the operation of ablation procedures through monitoring any number of chosen variables (e.g., temperature of the ablation electrode, ablation energy, and position of the assembly), assist in manipulation of the assembly during use, and provide the requisite energy source delivered to the electrode assembly 10. The present embodiments describe RF ablation electrode assemblies and methods, but it is contemplated that the present invention is equally applicable to any number of other ablation electrode assemblies where the temperature of the device and the targeted tissue areas is a factor during the procedure.

FIG. 1 is a general perspective view of an irrigated ablation catheter assembly having an RF generator assembly 14 and a fluid pump assembly 15 operably connected to an irrigation catheter 12 assembly having an irrigated electrode assembly 10 according to the present invention operably attached thereto. The structural and functional features of the catheter assembly 12 and the RF generator assembly 14 and pump assembly 15 are well-known to those of skill in the art. For example, the RF generator assembly could be an IBI-1500T RF Cardiac Ablation Generator available from Irvine Biomedical, Inc. in Irvine, Calif. 92614. The RF generator assembly could also be any other known assembly, including, for example, a Stockert RF generator available from Biosense, or one of the Atakr® series of RF generators available from Medtronic. The pump assembly can be any known assembly, including fixed volume rolling pumps, variable volume syringe pumps, and any other pump assembly known to those of skill in the art. FIGS. 2-12, discussed in more detail below, exemplify various embodiments of the irrigated ablation electrode assembly 10 according to the present invention.

Figure 2:
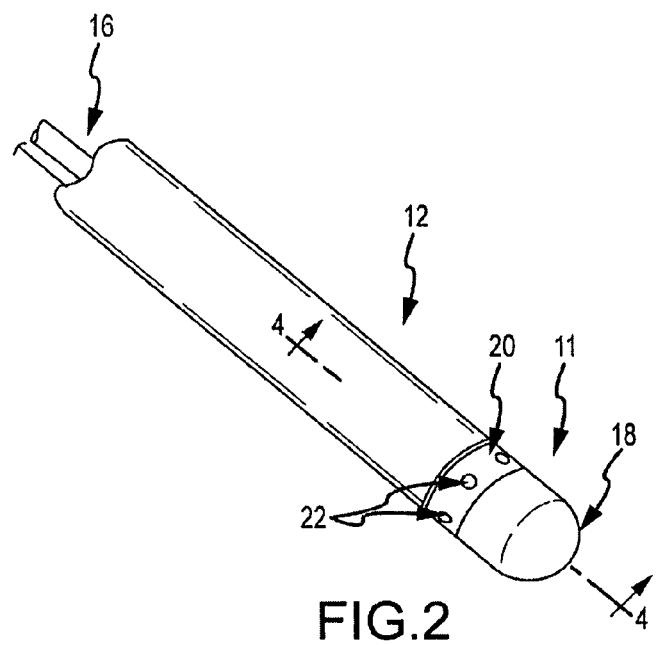
FIG. 2 is an enlarged, isometric view of the ablation electrode assembly according to an embodiment of the present invention operably connected to an irrigated catheter assembly.

FIG. 2 is an isometric view of an ablation electrode assembly 11 connected to an irrigated ablation catheter assembly 12 having a fluid delivery tube 16 therein. The ablation electrode assembly 11 generally comprises an irrigation member 20 and an ablation electrode member 18. The orientation of the members 18, 20 are generally such that the ablation electrode assembly 18 is situated at the distal end of the assembly with the irrigation member 20 located at the proximal end of the assembly, although it is conceivable the orientation could be reversed. The proximal member 20 has at least one passageway 24 (see FIG. 4) and at least one outlet 22 for delivery of a fluid to targeted tissue areas and the outside of the electrode assembly 11. The distal member 18 further comprises at least one temperature sensing mechanism 26 (see FIG. 4) disposed therein and operably connected to the RF generator assembly 14. The distal member 18 is comprised of any electrically, and potentially thermally, conductive material known to those of ordinary skill in the art for delivery of ablative energy to target tissue areas. Examples of the electrically conductive material include gold, platinum, iridium, palladium, stainless steel, and any mixtures thereof. Moreover, there are a number of electrode designs contemplated within the scope of the present invention including tip electrodes, ring electrodes, and any combination thereof.

In general accordance with the embodiments described herein, the fluid passageway(s) 24 and outlet(s) 22 are separated from the distal member 18, and accordingly the temperature sensing mechanism 26, by at least one poor thermally conductive material. A poor thermally conductive material is one with physical attributes that decrease heat transfer from the passageway(s) 24 to the distal member 18 by about 10% or more, and more preferably by about 25% or more measured by known methods to one of ordinary skill in the art. In particular embodiments, materials that decreased heat transfer by more than approximately 75% performed favorably. It is further contemplated that a poor thermally conductive material could have physical attributes that decrease heat transfer less than about 10%, provided that the remaining structural components are selected with the appropriate characteristics and sensitivities to maintain adequate monitoring and control of the process. Thus, while these properties are preferred, the poor thermally conductive material may be any material known to one of skill in the art consistent with the spirit of the invention. Examples of poor thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof.

As shown in more detail with respect to specific embodiments below, the poor thermally conductive material may be the material comprising the proximal member 20, or the distal member 18, a separate material from the proximal member 20 and the distal member 18, or any combination thereof. Additionally, the passageway(s) 24 and outlet(s) 22 defined by the proximal member 18 may also be separated longitudinally from the end 46 (see FIG. 3) of the distal member 18 thereby providing the benefit of insulating the passageway(s) 24 from the temperature sensor(s) 26 for improved temperature monitoring of the ablated target area during operation. The poor thermally conductive material, and the separation from the end 46 of the distal member 18, serve individually, and cooperatively, to minimize the effect of the lower temperature of the fluid delivered through the passageway(s) 24 and outlet(s) 22 from the temperature sensing mechanism(s) 26 within the distal member 18. The separation of the passageway(s) 24 and outlet(s) 22 from the distal member 18, and more particularly the temperature sensing mechanism 26, facilitate the dual purposes of (1) effectively irrigating the electrode assembly 10 and the targeted tissue area to minimize coagulation and unwanted tissue damage and (2) effectively controlling the operation of the ablation electrode assembly 10 in accordance with objects of the present invention.

Figure 3:
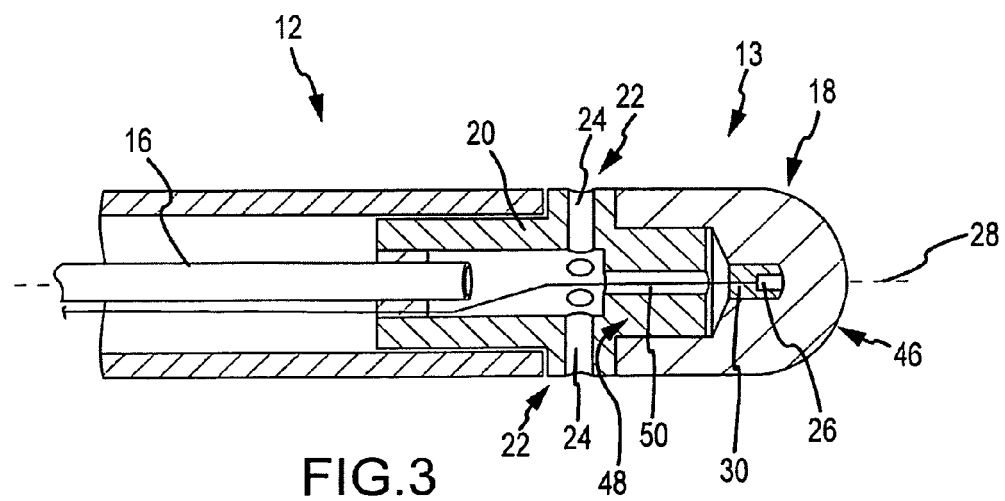
FIG. 3 is a cross-sectional view of an ablation electrode assembly according to an embodiment of the present invention.

FIG. 3 is a cross-sectional view of an embodiment of the ablation electrode assembly 13. FIG. 3 describes what is known to those in the art as a 2½ mm (length) ablation electrode assembly 10. A 2½ mm ablation electrode assembly 10 is often beneficial because it requires less power (around 10-20 W, as compared to around 20-40 W for a 4 mm assembly). However, it is contemplated that any size ablation electrode assembly 13, including a 4 mm assembly, is equally technically acceptable. In instances where a larger ablation area is desired to provide for different spatial orientation of the electrode assembly 13, a larger electrode surface area can be accommodated, while still yielding the desirable separation between the cooling passageways 24 and the temperature sensing mechanism 26.

As shown in FIG. 3, an ablation electrode assembly 13 is connected to an irrigation catheter assembly 12 having a fluid delivery tube 16. The ablation electrode assembly 13 comprises a proximal member 20, or manifold, a distal member 18, and a temperature sensing mechanism 26 operably connected to the RF generator assembly 14 (see FIG. 1). In this embodiment, the proximal member 20 itself is comprised of a poor thermally conducting material that serves to insulate the fluid from the remaining portions of the assembly 13. Preferably the proximal member 20 is made from a poor thermally conductive polymer, more preferably from a polyether ether ketone ("PEEK") because of this material's combination of thermal and physical properties. The proximal member 20 is configured to receive the fluid tube 16 of the catheter assembly 12 and comprises a plurality of passageways 24 extending from a central axis 28 of the assembly 13 axially toward the outer portion of the proximal member 20 terminating in corresponding outlets 22. Preferably, the plurality of passageways 24 are equally distributed around the proximal member 20 so as to provide equal distribution of fluid to the targeted tissue area and the outside of the assembly 13. The passageway 24 may be a single, annular passageway, or a number of individual passageways equally distributed around the proximal member 20. In this embodiment, the passageways 24 are at an angle substantially perpendicular to the longitudinal axis 28 of the assembly 13. In operation, fluid is pumped through the delivery tube 16 and passes through the passageways 24 and through the outlets 22 where it contacts with targeted tissue areas and the outside portion of the ablation electrode assembly 13.

The proximal member 20 is further configured to extend a portion 48 into the distal member 18 and has a pathway 50 for passage of the operable connection of the temperature sensing mechanism 26 within the distal tip 18. In this embodiment, this path 50 is shown extending substantially through the middle of the proximal member 20, but this path 50 can be located anywhere within or outside the proximal member 20. The resulting cross-sectional shape is substantially cross-shaped, in which the fluid passageways 24 and outlets 22 are isolated from other portions of the assembly 13 by the proximal member 20.

The distal member 18 of the ablation electrode assembly 13 has a generally cylindrical shape terminating in a hemispherical end. The distal member 18 is configured to accept a portion 48 of the proximal member 20 for attachment thereto. The distal member 18 may be connected to the proximal member 20 by any known mechanism including adhesives, press-fit configurations, snap-fit configurations, or the like.

The distal member 18 further contains at least one temperature sensing mechanism 26 disposed therein for measurement and control of the assembly 13 and targeted tissue areas during operation. It is further contemplated that additional temperature sensing mechanisms can be utilized for further control and monitoring of the temperature of the assembly 13 at various additional locations. For purposes of the present invention, the temperature sensing mechanism(s) 26 can be any mechanism known to one of skill in the art, including for example, thermocouples or thermistors. In a further embodiment, the temperature sensing mechanism 26 is surrounded, or encapsulated, by a second thermally conductive and electrically non-conductive material 30. This thermally conductive and electrically non-conductive material 30 serves to hold the temperature sensing mechanism 26 in place within the distal tip 18 and provides excellent heat exchange between the temperature sensing mechanism 26 and the distal member. This material 30 may be comprised of a number of materials known to one of skill in the art, including for example, thermally conductive resins, epoxies, or potting compounds, such as the material sold under the trademark STYCAST 2651 MM.

Figure 4:
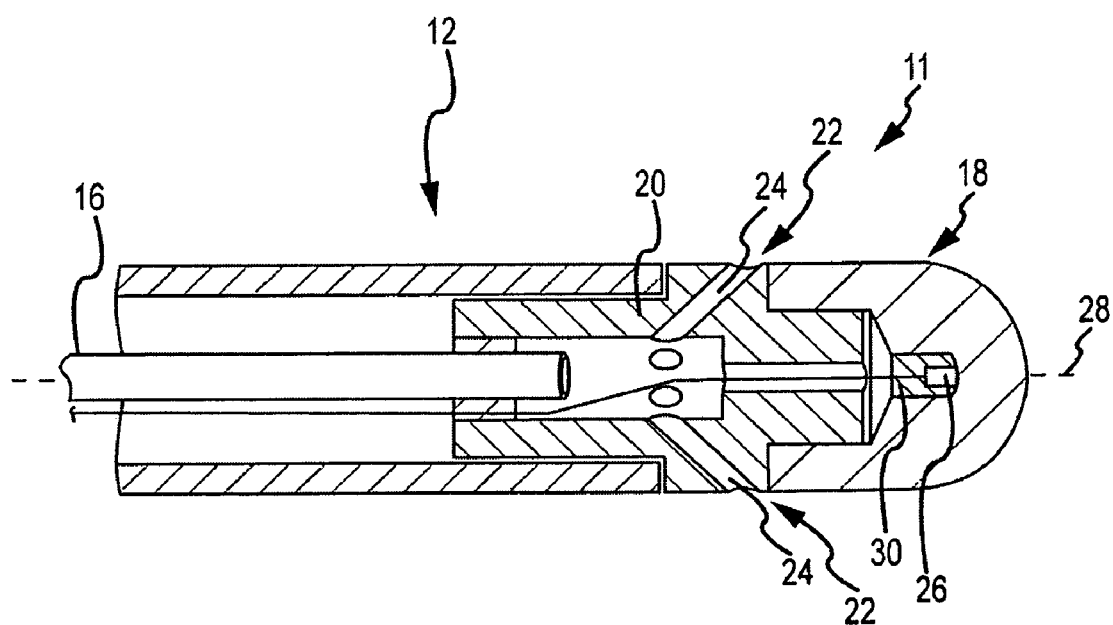
FIG. 4 is a cross-sectional view of the ablation electrode assembly of FIG. 2 taken along line 4-4 of FIG. 2.

FIG. 4 is a cross-sectional view of the ablation electrode assembly 11 of FIG. 2. In this embodiment, the fluid delivery conduits 24, or passageways, extend at an angle substantially less than perpendicular to the longitudinal axis 28. Angling of the passageways 24 away from perpendicular, but less than parallel, further assists in the delivery of the fluid to the targeted tissue areas, further decreases the risk of coagulation of the bodily fluids during ablation procedures, and allows for improved measurement and control of the ablation assembly 11 during operation. More specifically, the passageways 24 are oriented to direct irrigation fluid flow at the target area adjacent, preferably immediately adjacent, the intersection between the proximal member 20 and the distal member 18 (unlike the passageways 24 in FIG. 3 which do not direct irrigation fluid flow at the target area adjacent the intersection). Blood coagulation is more likely to occur in the target area due to a sharp rise in RF intensity, material discontinuity, and potentially geometric discontinuity caused by manufacturing imperfection in joining the proximal member 20 and the distal member 18. In specific embodiments, the passageways 24 extend at an angle between approximately 20 and 70 degrees, preferably at an angle between approximately 30 and 60 degrees, and more preferably at an angle of approximately 30 degrees. It is also contemplated that the passageways may be further angled in a second dimension, such that the passageways and orifices are configured to provide fluid to the external portion of the assembly in a swirling, or helical fashion. This configuration also serves to keep the fluid in closer proximity to the electrode assembly, thereby further preventing against coagulation during operation.

Again, in this embodiment, the temperature sensing mechanism 26 is surrounded, or encapsulated, by a second thermally conductive and electrically non-conductive material 30. This thermally conductive and electrically non-conductive material 30 serves to hold the temperature sensing mechanism 26 in place within the distal tip 28 and provides excellent heat exchange between the temperature sensing mechanism 26 and the distal member. This material 30 may be comprised of a number of materials known to one of skill in the art, including for example, thermally conductive resins, epoxies, or potting compounds, such as the material sold under the trademark STYCAST 2651 MM. By placing the temperature sensing mechanism 26 within the distal member 18, displaced from the proximal member 20, improved temperature measurements and control are still maintained, while allowing for decreased coagulation and unnecessary tissue damage through irrigation. This particular configuration enables the use of a number of different sizes of ablation electrodes 10, including 4 mm electrodes, ring electrodes, and combinations thereof.

Figure 5:
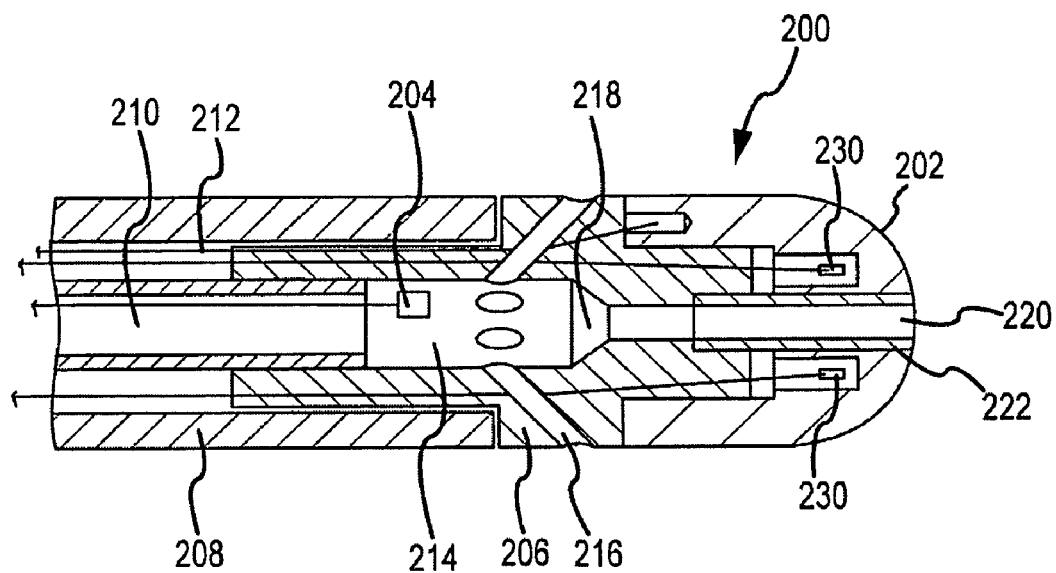
FIG. 5 is a cross-sectional view of an ablation electrode assembly according to another embodiment of the present invention.

FIG. 5 shows an ablation electrode assembly 200 having a distal member 202, a pressure sensor 204, a proximal member 206, a catheter shaft 208, and a fluid tube 210. The embodiment of FIG. 5 differs from the one in FIG. 4 in that the ablation electrode assembly 200 further includes a distal irrigation flow path 220 through the distal electrode 202. The fluid tube 210 which is typically a flexible tube has a lumen that is connected to the lumen or cavity 214 of the proximal member or manifold 206. A plurality of proximal irrigation flow passageways 216 extend from the lumen 214 to the exterior. The proximal passageways 216 preferably are angled toward the area of intersection between the proximal member 206 and the distal member 202. The lumen 214 may include a tapered lumen transition 218 between the larger diameter of the proximal portion of the lumen 214 and the distal portion of the lumen 214 that matches the size of the distal flow path 220 of the distal member 202. The pressure sensor 204 may be disposed in the lumen 214 in fluidic communication with the irrigation passageways 216. The catheter shaft 208 is connected to the proximal member 206 and is external to the fluid tube 210. The proximal member 206 is connected to the distal electrode 202. A power wire 212 supplies power to the distal electrode 202.

The distal flow path 220 extends longitudinally along the axis of the ablation electrode assembly 200. One or more temperature sensors 230 are provided in the distal member 202. While the temperature sensor in the embodiments of FIGS. 3 and 4 is disposed along the longitudinal axis of the distal electrode, the temperature sensors 230 in this embodiment is disposed slightly off-axis due to the presence of the distal flow path 220. If there are multiple temperature sensors 230, they are preferably uniformly spaced circumferentially with respect to the longitudinal axis of the distal member 202.

An insulative lining 222 having poor thermal conductivity (preferably substantially lower than the thermal conductivity of the material of the distal member 202) insulates the distal passage 220 from the distal member 202 and from the temperature sensors 230. The proximal member 206 is also made of a material of poor thermal conductivity, and serves to separate the electrode 202 from the fluid tube 210 and the proximal irrigation flow passageways 216. The fluid paths do not come into contact with any portion, particularly any interior portion, of the distal electrode 202. As such, within the ablation electrode assembly 200, the irrigation flow is thermally insulated from the distal electrode 202 and the temperature sensors 230 by distance and material of poor conductivity. The proximal member 206 and the insulative lining 222 may be made of a variety of materials that have insulating properties such as, for example, DELRIN®, polyetheretherketone (PEEK), and high-density polyethylene (HDPE).

The pressure sensor 204 may be suspended in the inner cavity or lumen 214. Alternatively, the pressure sensor may be mounted inside the inner cavity 214. The pressure sensor 204 measures the pressure of fluid inside the electrode 202. The size of the pressure sensor is preferably minimized so as not to impede fluid flow inside the catheter. This pressure measurement is relayed to the outside. In one embodiment of the invention, this pressure measurement is relayed to the outside via a relay cable. In another embodiment of the invention, this pressure measurement is relayed to the outside wirelessly. In another embodiment of the invention, the pressure measurement may be relayed to a computational device (such as e.g., a personal computer) that also controls the flow of energy into electrode 202.

The pressure sensor 204 may be a fiber optic pressure sensor, which relays pressure measurements to the outside via use of a fiber optic cable. Such a fiber optic pressure sensor may be as small as 0.5 mm in width and only a few nanometers long. The fiber optic cable may be as small as 0.17 mm in diameter. The fiber optic pressure sensor may be one of the commercially available sensors such as the FOBPS family of fiber optic pressure sensors by World Precision Instruments (description available online at http://www.wpiinc.com/WPI_Web/Animal-Phy/BP_Temp_sensor/BP_Temp_Sensor.html, last visited Nov. 11, 2006). This pressure sensor may be operably linked to the electrode.

An open irrigation catheter according to the instant disclosure can be operated with a fixed flow rate of cooling fluid inside the catheter (a so-called fixed flow condition). Thus, when an open irrigated ablation catheter has contact with tissue, some of the plurality of openings on the distal electrode will be plugged by the tissue. The pressure inside the electrode will increase as a function of the reduced open irrigation area as well as the fixed flow condition. When the catheter contacts target tissue, one or more of plurality of passages are blocked by the tissue. Thus, the pressure inside the catheter will increase. This increase in pressure is then detected by the pressure sensor. Based on this increase in pressure, an operator of the catheter will then recognize that tissue contact has been made and ablation can proceed. Alternatively, the increase in pressure is operatively linked to the electrode. Thus, upon an increase in pressure, the electrode will be triggered automatically.

Figure 6:
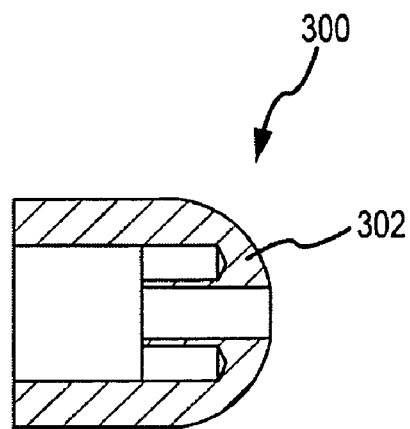
FIG. 6 is a cross-sectional view of a distal ablation electrode having a non-hemispherical surface according to another embodiment of the invention.

The distal electrodes 18, 202 of FIGS. 3-5 have hemispherical surfaces. Different geometries for the distal electrode may be more suitable for certain applications depending on the location and shape of the target tissue, the manner of access to the target tissue, and the desired ablation characteristics such as shape and size of the ablation. FIG. 6 shows a distal electrode 302 of an ablation electrode assembly 300 having a non-hemispherical surface. The surface of the distal electrode 300 is rounded, but the radius of curvature of the rounded surface is different from (in this case smaller than) the radius of the circular cylindrical portion of the distal electrode 300. In addition, the center of the radius of curvature does not lie along the longitudinal axis of the distal electrode 300, but is disposed at a distance spaced from the longitudinal axis.

Figure 7:
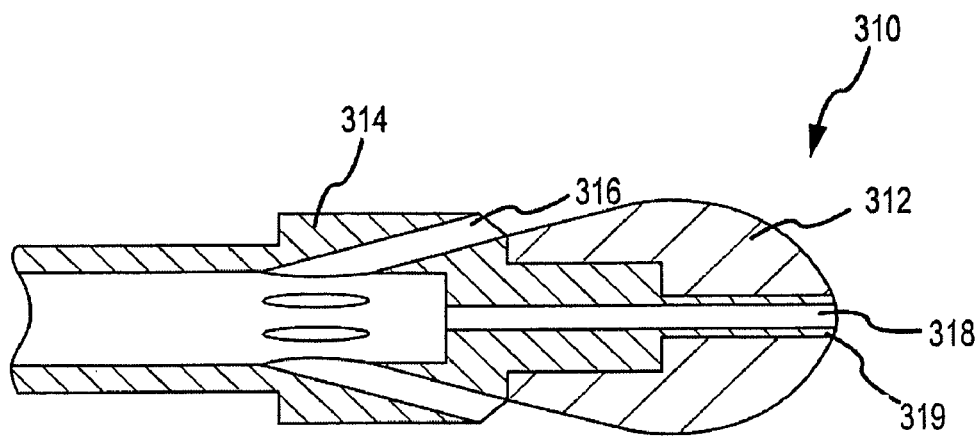
FIGS. 7-12 are cross-sectional views of ablation electrode assemblies according to additional embodiments of the invention.

FIG. 7 shows another ablation electrode assembly 310 having a distal electrode 312 and a proximal member 314 which has irrigation passageways 316. The distal surface of the distal electrode 312 is generally elliptical while the proximal surface of the distal electrode 312 is tapered or slanted. The angle of the slanted surface is similar to the angle of the irrigation passageways 316, which is about 15 degrees. The maximum diameter of the distal member is equal to or larger than the maximum diameter of the proximal member. Again, the irrigated passageways 316 are oriented to direct irrigation fluid flow adjacent, preferably immediately adjacent, the intersection between the proximal member 314 and the distal member 312. The distal irrigation path 318 is lined with an insulative member 319, which may be a separate lining or formed as a part of the proximal member 314. One or more temperature sensors similar to those shown in FIG. 5 may be provided in the distal member 312.

Figure 8:
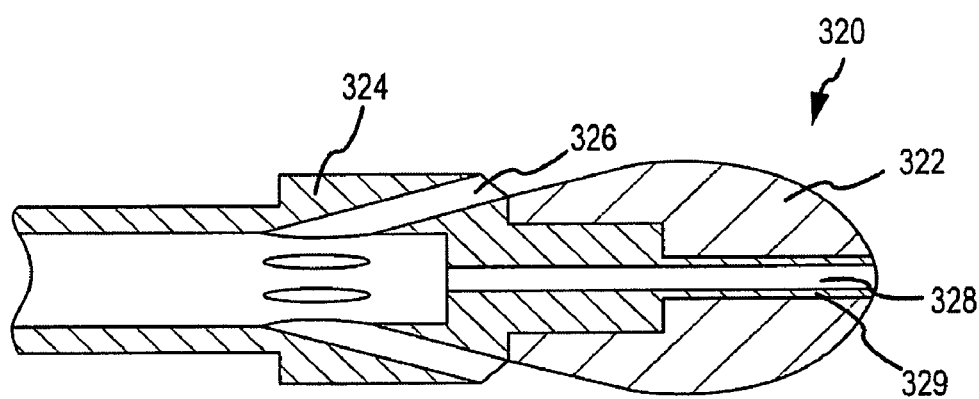

FIG. 8 shows another ablation electrode assembly 320 having a distal electrode 322 and a proximal member 324 which has irrigation passageways 326. The distal surface of the distal electrode 322 is generally elliptical while the proximal surface of the distal electrode 322 is tapered or slanted. The proximal portion of the distal electrode 322 in this embodiment is more elongated than that of the distal electrode 312 in FIG. 7, up to about 4 mm. The distal irrigation path 328 is lined with an insulative member 329, which may be a separate lining or formed as a part of the proximal member 324. One or more temperature sensors similar to those shown in FIG. 5 may be provided in the distal member 322.

Figure 9:
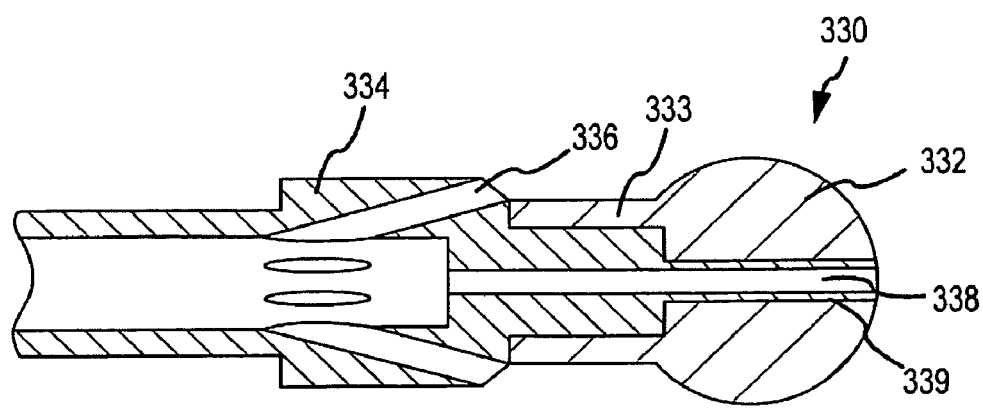

FIG. 9 shows another ablation electrode assembly 330 having a distal electrode 332 and a proximal member 334 which has irrigation passageways 336. The distal electrode 332 has a generally spherical surface which transitions to a narrower circular cylindrical neck 333 in the proximal portion. The angle of the irrigation passageways 336 is about 15 degrees. The maximum diameter of the distal member is equal to or larger than the maximum diameter of the proximal member. The irrigated passageways 336 are oriented to direct irrigation fluid flow adjacent, preferably immediately adjacent, the intersection between the proximal member 334 and the distal member 332. The distal irrigation path 338 is lined with an insulative member 339, which may be a separate lining or formed as a part of the proximal member 334. One or more temperature sensors similar to those shown in FIG. 5 may be provided in the distal member 332.

Figure 10:
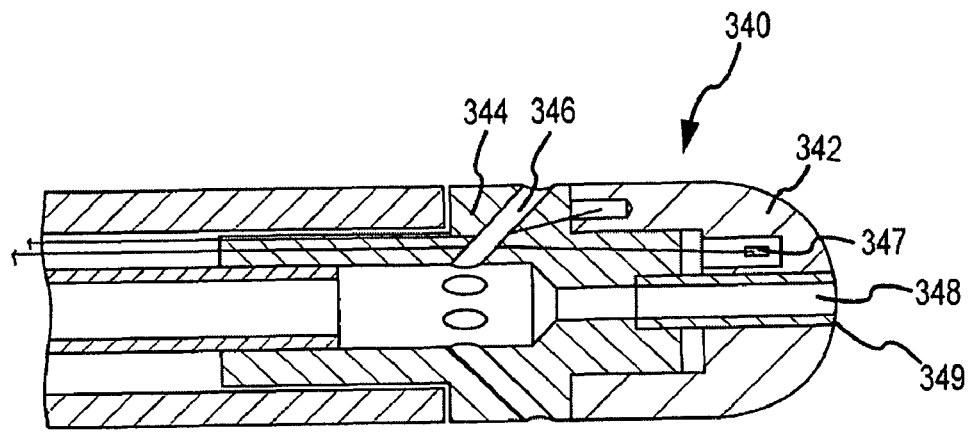

FIG. 10 shows another ablation electrode assembly 340 having a distal electrode 342 and a proximal member 344 which has irrigation passageways 346. The distal surface of the distal electrode 342 has a generally flat tip in the center region and a substantial rounded edge portion surrounding the generally flat center region. The proximal surface of the distal electrode 342 is circular cylindrical. The angle of the irrigation passageways 346 is about 30 degrees. The irrigated passageways 346 are oriented to direct irrigation fluid flow adjacent, preferably immediately adjacent, the intersection between the proximal member 344 and the distal member 342. The distal irrigation path 348 is lined with an insulative member 349. One or more temperature sensors 347 may be provided in the distal member 342.

Figure 11:
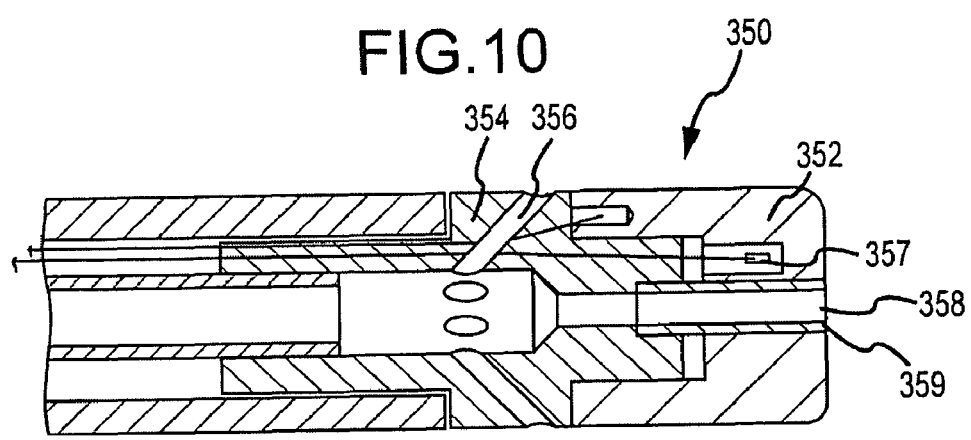

FIG. 11 shows another ablation electrode assembly 350 having a distal electrode 352 and a proximal member 354 which has irrigation passageways 356. The distal surface of the distal electrode 352 has a generally flat tip in the center region and a small rounded edge portion surrounding the generally flat center region, so that almost the entire tip of the distal electrode 352 is generally flat. The proximal surface of the distal electrode 352 is circular cylindrical. The angle of the irrigation passageways 356 is about 30 degrees. The irrigated passageways 356 are oriented to direct irrigation fluid flow adjacent, preferably immediately adjacent, the intersection between the proximal member 354 and the distal member 352. The distal irrigation path 358 is lined with an insulative member 359. One or more temperature sensors 357 may be provided in the distal member 352.

Figure 12:
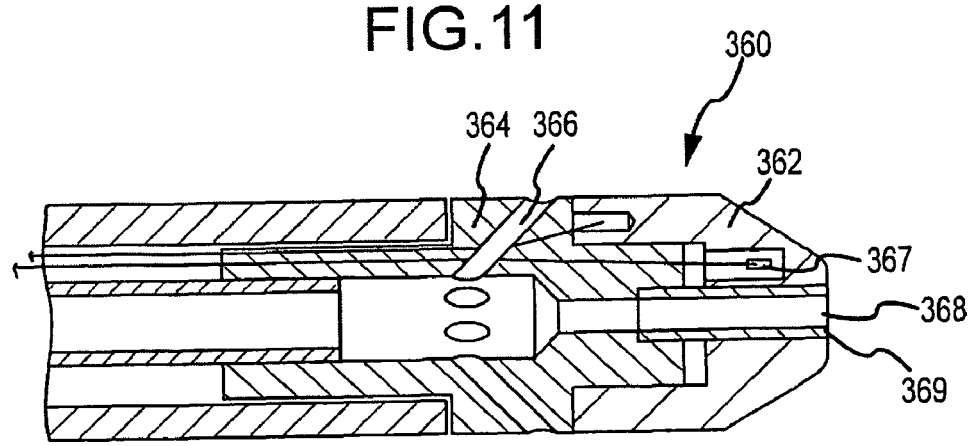

FIG. 12 shows another ablation electrode assembly 360 having a distal electrode 362 and a proximal member 364 which has irrigation passageways 366. The distal surface of the distal electrode 362 has a generally flat tip in the center region and a chamfered edge portion surrounding the generally flat center region. The proximal surface of the distal electrode 362 is circular cylindrical. The angle of the irrigation passageways 366 is about 30 degrees. The irrigated passageways 366 are oriented to direct irrigation fluid flow adjacent, preferably immediately adjacent, the intersection between the proximal member 364 and the distal member 362. The distal irrigation path 368 is lined with an insulative member 369. One or more temperature sensors 367 may be provided in the distal member 362.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation electrode assembly for use with an irrigated catheter device, the irrigated ablation electrode assembly comprising:
   a proximal member having at least one passageway for a fluid with an outlet disposed at an external surface of the proximal member; and
   a distal member connected with the proximal member and having an external surface, a first end, and a second end, wherein one of the first end and the second end of the distal member is configured to receive a portion of the proximal member such that the portion of the proximal member is disposed internally relative to the distal member, the distal member including an electrode;
   wherein the external surface of the proximal member and the external surface of the distal member meet at an intersection;
   wherein the at least one passageway of the proximal member is configured to direct a fluid flow through the outlet toward a region adjacent the intersection; and
   wherein the at least one passageway and the outlet are not positioned longitudinally between the first end and the second end of the distal member.

2. The irrigated ablation electrode assembly of claim 1 wherein the proximal member comprises a material having a thermal conductivity which is lower than a thermal conductivity of a material of the distal member.

3. The irrigated ablation electrode assembly of claim 1 wherein the distal member comprises an electrically conductive material.

4. The irrigated ablation electrode assembly of claim 1 wherein the proximal member comprise an electrically non-conductive material.

5. The irrigated ablation electrode assembly of claim 1 wherein the at least one passageway extends toward the distal member at an angle which is greater than 0 degree and less than 90 degrees with respect to a longitudinal axis of the proximal member.

6. The irrigated ablation electrode assembly of claim 5 wherein the at least one passageway extends toward the distal member at an angle between approximately 15 degrees and approximately 70 degrees with respect to the longitudinal axis of the proximal member.

7. The irrigated ablation electrode assembly of claim 1 wherein the proximal member comprises a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof.

8. The irrigated ablation electrode assembly of claim 1 wherein the distal member comprises a material selected from the group consisting of platinum, gold, iridium, stainless steel, palladium and mixtures thereof.

9. The irrigated ablation electrode assembly of claim 1 wherein the distal member includes a distal flow path extending along a longitudinal axis of the distal member.

10. The irrigated ablation electrode assembly of claim 9 further comprising an insulative lining surrounding the distal flow path and separating the distal flow path from the distal member, the insulative lining comprising a material having a thermal conductivity which is lower than a thermal conductivity of a material of the distal member.

11. The irrigated ablation electrode assembly of claim 10 wherein the insulative lining comprises a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof.

12. The irrigated ablation electrode assembly of claim 1 further comprising at least one temperature sensor disposed in the distal member.

13. The irrigated ablation electrode assembly of claim 1 wherein the distal member has an external surface that includes a rounded distal portion that is non-spherical and a circular cylindrical proximal portion.

14. The irrigated ablation electrode assembly of claim 1 wherein the at least one passageway extends toward the distal member at a first angle relative to a central axis of the assembly and wherein the distal member has an external surface that includes a generally elliptical distal portion and a tapered proximal portion narrowing toward the proximal member, wherein the external surface of the tapered proximal portion is disposed at substantially the same relative orientation as the first angle.

15. The irrigated ablation electrode assembly of claim 1 wherein the distal member has an external surface that includes a generally spherical distal portion and a proximal neck portion that is circular cylindrical and narrower than the generally spherical distal portion, wherein the proximal neck portion of the distal member has a smaller outer diameter than a portion of the proximal member in which the at least one passageway is disposed and wherein the outlet of the at least one passageway is disposed at the intersection.

16. The irrigated ablation electrode assembly of claim 1 wherein the distal member has an external surface that includes a generally flat tip surrounded by a rounded edge portion and a circular cylindrical proximal portion.

17. The irrigated ablation electrode assembly of claim 1 wherein the distal member has an external surface that includes a generally flat tip surrounded by a chamfered edge portion and a circular cylindrical proximal portion.

18. The irrigated ablation electrode assembly of claim 1 wherein the proximal member includes a plurality of passageways distributed generally uniformly in a circumferential direction of the proximal member.

19. The irrigated ablation electrode assembly of claim 1 wherein the at least one passageway of the proximal member does not come into contact with any interior portion of the distal member.

20. The irrigated ablation electrode assembly of claim 1 wherein a maximum diameter of the distal member is equal to or larger than a maximum diameter of the proximal member.

21. An irrigated ablation electrode assembly for use with an irrigated catheter device, the irrigated ablation electrode assembly comprising:
　a proximal member having an external surface;
　a distal member connected with the proximal member and having an external surface, a first end, and a second end, wherein one of the first end and the second end of the distal member is configured to receive a portion of the proximal member such that the portion of the proximal member is disposed internally relative to the distal member, the distal member including an electrode; and
　at least one passageway within the irrigated ablation electrode assembly having an outlet for a fluid;
　wherein the external surface of the proximal member and the external surface of the distal member meet at an intersection;
　wherein the at least one passageway is configured to direct a fluid flow through the outlet toward a region adjacent the intersection; and
　wherein the at least one passageway and the outlet are not positioned longitudinally between the first end and the second end of the distal member.

22. The irrigated ablation electrode assembly of claim 21 wherein the at least one passageway does not come into contact with any interior portion of the distal member.

23. The irrigated ablation electrode assembly of claim 21 wherein the at least one passageway is thermally insulated from the distal member by a poor thermal conductive material which is lower in thermal conductivity than a material of the distal member.

24. A method for irrigated ablation of tissue, the method comprising:
　flowing a fluid to an irrigated ablation electrode assembly which includes a proximal member having at least one passageway for the fluid with an outlet disposed at an external surface of the proximal member, and a distal member connected with the proximal member and having an external surface, a first end, and a second end, wherein one of the first end and the second end of the distal member is configured to receive a portion of the proximal member such that the portion of the proximal member is disposed internally relative to the distal member, the distal member including an electrode, wherein the at least one passageway and the outlet are not positioned longitudinally between the first end and the second end of the distal member, and wherein the external surface of the proximal member and the external surface of the distal member meet at an intersection; and
　directing the fluid flow through the at least one passageway of the proximal member through the outlet toward a region adjacent the intersection.

\* \* \* \* \*